(12) United States Patent
Shofner et al.

(10) Patent No.: US 7,257,543 B2
(45) Date of Patent: Aug. 14, 2007

(54) SYSTEM AND METHOD FOR MARKETING COTTON

(75) Inventors: Christopher K. Shofner, Knoxville, TN (US); Frederick M. Shofner, Knoxville, TN (US)

(73) Assignee: Shofner Engineering Associates, Inc., Knoxville, TN (US)

(*) Notice: Subject to any disclaimer, the term of this patent is extended or adjusted under 35 U.S.C. 154(b) by 896 days.

(21) Appl. No.: 09/917,186

(22) Filed: Jul. 27, 2001

(65) Prior Publication Data

US 2002/0029151 A1    Mar. 7, 2002

Related U.S. Application Data

(60) Provisional application No. 60/227,211, filed on Aug. 23, 2000, provisional application No. 60/221,104, filed on Jul. 27, 2000.

(51) Int. Cl.
*G06Q 99/00* (2006.01)
*G06Q 30/00* (2006.01)
*G06F 19/00* (2006.01)

(52) U.S. Cl. ............................ 705/1; 705/26; 700/142
(58) Field of Classification Search ................ 705/1, 705/400; 356/245
See application file for complete search history.

(56) References Cited

U.S. PATENT DOCUMENTS

| | | | |
|---|---|---|---|
| 5,063,507 A | * | 11/1991 | Lindsey et al. ............... 705/26 |
| 5,285,383 A | | 2/1994 | Lindsey et al. |
| 5,805,452 A | * | 9/1998 | Anthony et al. ............ 700/142 |
| 5,960,411 A | | 9/1999 | Hartman et al. |
| 6,035,288 A | | 3/2000 | Soloman |
| 6,085,176 A | | 7/2000 | Woolston |
| 6,092,069 A | | 7/2000 | Johnson et al. |
| 6,484,149 B1 | * | 11/2002 | Jammes et al. ............... 705/26 |
| 2001/0011244 A1 | | 8/2001 | Evans .......................... 705/37 |

FOREIGN PATENT DOCUMENTS

| | | | |
|---|---|---|---|
| DE | 002017546 | * | 4/1970 |
| WO | WO02/11032 | * | 2/2002 |

OTHER PUBLICATIONS

"IntelliGin—Improved Cotton Ginning Technology." Weaver, Tara, Argicultural Research, p. 15 Feb. 1998.*
F. M. Shofner and C. K. Shofner, "Cotton Classing in the New Millennium", 25th International Cotton Conference, Bremen, Germany, Mar. 1-4, 2000.

* cited by examiner

*Primary Examiner*—John W. Hayes
*Assistant Examiner*—Rutao Wu
(74) *Attorney, Agent, or Firm*—Carter Schnedler & Monteith, P.A.

(57) ABSTRACT

Computer-implemented systems and methods for building a database of bales of cotton available for sale, and for electronic commerce of bales of cotton. A fiber quality measurement instrument located in a cotton gin provides fiber quality data substantially concurrently with the making up of cotton into individual bales. The fiber quality measurement instrument is connected through a communications network, such as the internet, for uploading fiber quality data to a database storage device. For electronic commerce, a search engine is connected via the communications network to interrogate the database to select bales having fiber qualities within specified ranges for a candidate buyer.

32 Claims, 7 Drawing Sheets

PLEASE SELECT THE FIBER QUALITY DATA PRODUCTS
THAT ARE IMPORTANT FOR YOUR PRODUCT AND PROCESS

| Fiber Properties | select |
|---|---|
| mic | ☑ |
| length | ☑ |
| Length Unif | ☐ |
| sfc | ☑ |
| strength | ☐ |
| elongation | ☐ |
| ColorGrade | ☑ |
| rd | ☐ |
| b | ☐ |
| LeafCall | ☑ |
| area | ☐ |
| MoistureContent | ☐ |
| m_neps | ☐ |
| scf | ☐ |
| maturity | ☐ |
| fineness | ☐ |
| stickiness | ☐ |

Reset  Go

FIG.3

PLEASE DEFINE THE RANGE OF FIBER QUALITY MEASUREMENTS IMPORTANT TO YOUR PRODUCT AND PROCESS

| fieldname | Range | from | to |
|---|---|---|---|
| mic | (2,8) | 3 | 4 |
| length | (0.9,1.5) | 32 | 34 |
| sfc | (1,10) | 7 | 9 |
| ColorGrade | (11,85) | 21 | 51 |
| LeafCall | (1,7) | 2 | 4 |

Reset  Go

SYSTEM AND METHOD FOR MARKETING COTTON

CROSS-REFERENCE TO PROVISIONAL PATENT APPLICATIONS

The benefit of U.S. Provisional Patent Applications Ser. No. 60/221,104, filed Jul. 27, 2000, and Ser. No. 60/227,211, filed Aug. 23, 2000 is claimed.

BACKGROUND OF THE INVENTION

The invention relates generally to the marketing of cotton and, more particularly, to computer-implemented systems and methods for facilitating electronic commerce in cotton employing a database of bale identifications and associated fiber quality data.

Electronic commerce in cotton is known and currently practiced, with well-accepted advantages. One example of a system, implemented by Plains Cotton Cooperative Association, in Lubbock, Tex., is disclosed in Lindsey et al U.S. Pat. No. 5,285,383. In addition, the Staple Cotton Cooperative Association, headquartered in Greenwood, Miss., is currently engaged in electronic commerce of cotton employing a database.

Currently, whether cotton is subject to electronic commerce or not, harvested cotton is brought to a cotton gin. The gin processes the cotton, including removing seeds. Near the end of the process, the cotton enters a bale press, where the ginned cotton is compressed into bales. Each bale of cotton has dimensions of approximately 2×3×5 feet (60×90×150 cm), and a net weight of approximately 480 pounds (220 kg). Each bale is tagged with a Permanent Bale Identification (PBI) number, employing bar code technology, and then transported to a warehouse, or other storage facility.

Before the cotton can be marketed, the fiber quality must be measured. Cotton fiber quality is currently measured, or classified, by comparing either human or instrumental measurements of unknown samples to observations of or measurements on so-called cotton standards. Valuations of the cotton commodity, in transactions between willing sellers and willing buyers, typically either on a bale-by-bale basis or in fifty- to one hundred-bale lots, depend upon these classing measurements. Similarly, allocations and shipments and, ultimately, utilizations, depend upon these human and instrumental measurements of fiber qualities.

Thus, at the gin's bale press or, in some cases, at an on-site or off-site warehouse, samples are cut from two sides of each bale and are sent to a classing office (actually, a laboratory) to measure the fiber quality for purposes mentioned just above. These samples are referred to herein as bale classing samples. In the United States, the quality of a producer's cotton is determined by the U.S. Department of Agriculture Agricultural Marketing Service (USDA AMS). The USDA classing offices employ High Volume Instruments (HVIs) to measure the fiber qualities known as Micronaire, Length, Strength and Color. Human classer "measurements" are typically employed for the fiber quality known as Trash. In the United States, there are approximately eleven USDA classing offices, to which about 17,000,000 bale samples are sent for classing each year.

Cotton is an important commodity in world trade, and is bought and sold on the basis of US cents/pound for given fiber qualities. Fiber qualities are determined by cotton classing. Cotton classing in other countries typically uses USDA standard materials for both instrumental and human measurements, but the parties responsible for the classing function vary widely from country to country.

Accordingly, there is an inherent delay, typically around four days (two days for sample transportation, and two days for laboratory turnaround), between when a bale is produced at the gin and when fiber quality data are available so the bale can be marketed. This is so even in the cases of the electronic commerce systems implemented by Plains Cotton Cooperative Association and Staple Cotton Cooperative Association mentioned above. One adverse result of this delay is that physically relatively large warehouse and storage areas must be located at cotton gins or elsewhere in order to absorb (in effect, buffer) bales after they are made up but before their fiber qualities are known.

Moreover, since the fiber qualities of bales are not known prior to being transported to warehouses, bales having similar fiber qualities, and likely subsequently to be purchased as a lot once the fiber quality has been determined, are frequently scattered randomly about the warehouse or storage area. Later, when a lot of bales having similar fiber qualities is to be assembled for delivery to a buyer, a substantial and time-consuming effort may be devoted to physically locating and selecting the individual bales. Currently, it can cost US $5.00 or more per bale for random retrieval to locate and pick up a particular bale. A related adverse result of the delay in the availability of fiber quality data is that it is difficult for bales leaving the bale press and being transported to the warehouse or other storage facility to be designated for a particular buyer.

SUMMARY OF THE INVENTION

It is therefore seen to be desirable to facilitate the electronic commerce of cotton through efficient use of computer and communications network technology, implementing what may be termed a "digital cotton warehouse."

It is also seen to be desirable to provide systems and methods which facilitate the efficient movement and handling of individual physical bales of cotton through the entire transportation, storage and delivery process.

In one exemplary embodiment, a computer-implemented system for building a database of data describing individual bales of cotton available for sale includes a database storage device connected to a communications network for storing a database of bale identifications and associated fiber quality data, and a fiber quality measurement instrument located in a cotton gin for providing fiber quality data on bale classing samples cut from individual bales at a bale press substantially concurrently with the making up of cotton into individual bales. The fiber quality measurement instrument is connected to the communications network for uploading fiber quality data to the database storage device.

A related computer-implemented system for electronic commerce of bales of cotton comprises a database storage device connected to a communications network for storing the database of data describing individual bales of cotton, in particular, bale identifications and associated fiber quality data, as well as a fiber quality measurement instrument located in a cotton gin for providing fiber quality data on bale classing samples cut from individual bales at a bale press substantially concurrently with the making up of cotton into individual bales. Again, the fiber quality measurement instrument is connected to the communications network for uploading fiber quality data to the database storage device. The system for electronic commerce additionally includes a search engine connected via the communications network to interrogate the database to select bales having fiber qualities within specified ranges for a candidate buyer.

A corresponding computer-implemented method for building a database of bales of cotton available for sale comprises the steps of employing a fiber quality measurement instrument located in a cotton gin to provide fiber quality data on bale classing samples cut from individual bales at a bale press substantially concurrently with the making up of cotton into individual bales, and then transmitting the fiber quality data via a communications network to a database storage device that stores the database of bale identifications and associated fiber quality data.

A corresponding computer-implemented method for electronic commerce of bales of cotton comprises the steps of employing a fiber quality measurement instrument located in a cotton gin to provide fiber quality data on bale classing samples cut from individual bales at a bale press substantially concurrently with the making up of cotton into individual bales, then transmitting the fiber quality data via a communications network to the database storage device that stores the database of bale identifications and associated fiber quality data, and finally employing the search engine connected via the communications network to interrogate the database to select bales having fiber qualities within specified ranges for the candidate buyer.

DETAILED DESCRIPTION

Figure 1:
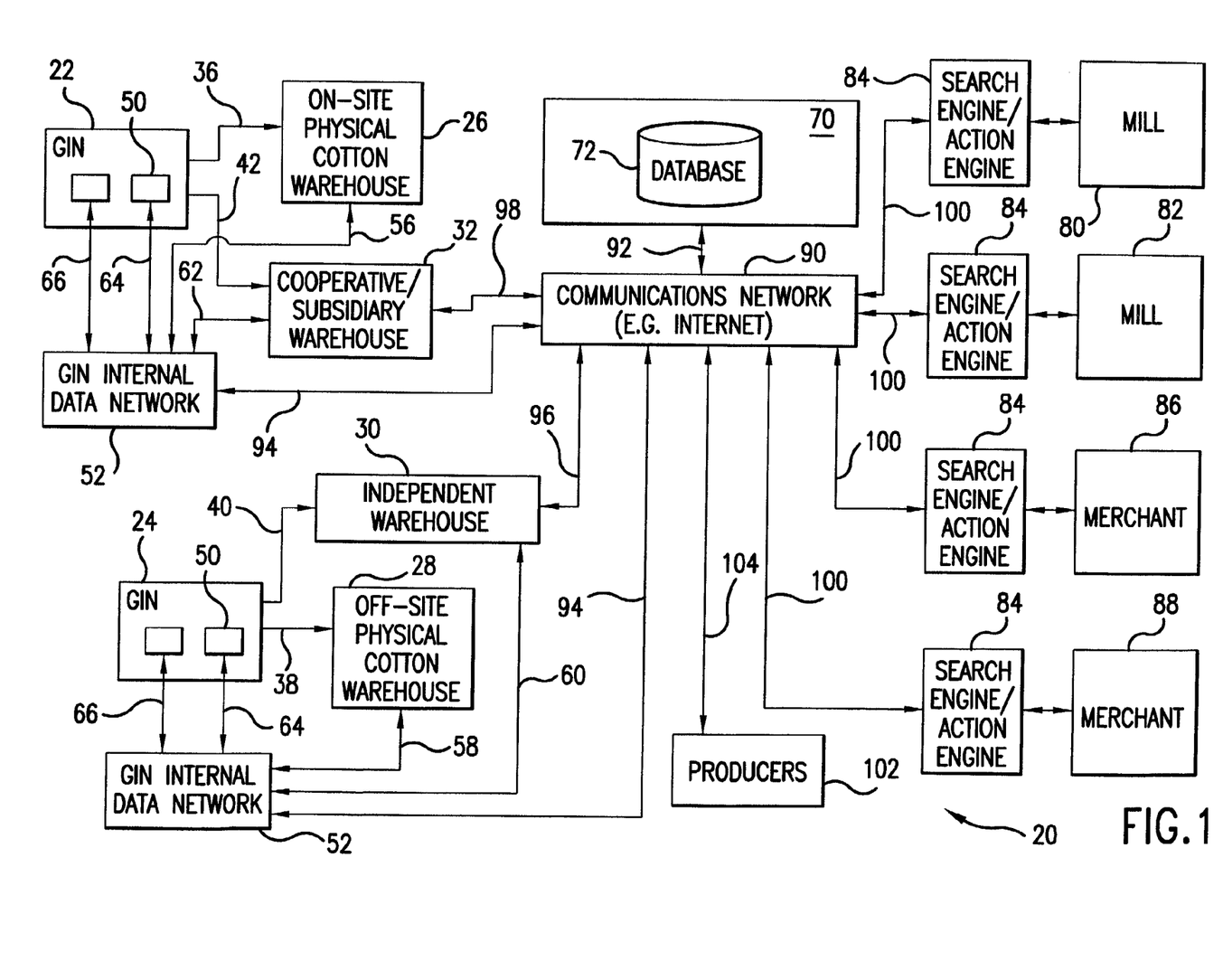
FIG. 1 is a block diagram of a system embodying the invention.

Referring first to the block diagram of FIG. 1, a system 20 embodying the invention includes, generally as a first element, a plurality of cotton gin facilities 22 and 24 and, for the physical storage of bales of cotton, associated exemplary on-site 26 or off-site 28 warehouses or other storage areas, such as independent 30 or cooperative/subsidiary 32 warehouses. As represented by arrows 36, 38, 40 and 42, bales of cotton are transported from bale presses (not shown) within the gin facilities 22 and 24 to the respective warehouses 26, 28, 30 and 32. Thus, various warehouse types are used for the storage of bales. On-site warehouses 26 are located on the gin property and are typically owned by the ginning firm. Off-site warehouses 28 are owned by the ginning firm, or by others independent of the ginning firm. Cooperative warehouses 32 are typically owned by a cooperative of producers and ginners. Independent warehouses 30 are owned by firms not directly involved with cotton production or ginning. Independent warehouses 30 include warehouses owned by merchant firms. Such merchant-owned, independent warehouses 30 can benefit significantly when embodiments of the invention are employed.

Within each gin facility 22 and 24 is a fiber quality measurement instrument 50. The fiber quality measurement instrument 50 provides fiber quality data substantially concurrently with the making up of cotton into individual bales. The term "substantially concurrently" is intended herein to mean within minutes of the making up of a bale of cotton at the bale press. Thus, conventional bale classing samples are cut from the sides of the bale right at the bale press, prior to wrapping the bale, and immediately delivered to the measurement instrument 50 for classing. Such measurements may be made with either manual or automatic versions of a particular fiber quality measurement instrument 50 identified below. In some cases, samples may be taken from the bale and fiber quality data measured immediately upon entering the warehouse 26 or 28. A characteristic of embodiments of the invention is immediacy of the classing data, in the gin, such that those data may be "fed forward" to optimize the marketing process. Another benefit of immediately available classing data in the gin is that the ginning process may also be optimized by "feed back" controls.

The fiber quality measurement instrument 50 may make the same fiber quality measurements currently made by centralized classing offices that employ High Volume Instruments (HVIs) or human Classers, which fiber qualities currently are Micronaire, Length, Strength, Color and Trash. Additional fiber qualities may be measured, including moisture content, nep content, maturity, fineness and stickiness. Importantly, images may be acquired.

One particularly suitable instrument 50 for this purpose is a stand alone instrument disclosed in our international patent application No. PCT/US 00/25470, published on 22 Mar. 2001 as No. WO 01/20321, titled "Conditioning and Testing Cotton Fiber," and also generally described in the invited paper F. M. Shofner and C. K. Shofner, "Cotton Classing in the New Millennium," 25th International Cotton Conference, Bremen, Germany, 1-4 Mar. 2000, currently known as "RapidTester." That international patent application No. PCT/US 00/25470 includes disclosure from concurrently-filed U.S. patent application Ser. No. 09/663,502, now U.S. Pat. No. 6,735,327, titled "Color and Trash Measurements by Image Analysis" (printed with the wrong Abstract), which also and more concisely discloses the "RapidTester" machine. "RapidTester" is a robust stand-alone platform, into which multiple fiber quality measurement modules are placed. The "RapidTester" instrument measures fiber qualities of cotton samples to produce multiple data products, including images, and additionally internally and ultra-rapidly conditions the samples so that fiber quality testing can be performed at so-called "Standard Conditions," in particular at 70° F. (21° C.) and 65% relative humidity.

Also associated with each gin facility 22 is a gin internal data network 52, including a computer system, which tracks individual bales within the gin facility 22 or 24 and associated warehouse 26 or 28, among other tasks, as is generally known. Warehousing operations are facilitated by bidirectional data communications lines 56, 58, 60 and 62 between the warehouses 26, 28, 30 and 32 and the gins 22, 24. Benefits include improved efficiencies in bale handling, reductions in transaction time and complexities, reductions in inventory time, increases in communications integrity, and the like. In embodiments of the invention, as represented by bidirectional data communications lines 64, fiber quality data, optionally including images, as determined by the fiber quality measurement instrument 50 is communicated to the gin internal data network 52.

In addition to fiber quality data as determined by the measurement instrument 50 based on bale samples, ginning process parameters such as critical temperatures, process throughput, number and type of seed cotton and lint cleaners, critical seed cotton and lint moisture contents, and other parameters determined to be relevant, are measured by other instruments collectively designated 66. The instruments 66 are connected bidirectionally to the gin internal data network 52 50 that ginning process parameter measurements determined by the instruments 66 are communicated to the gin internal data network 52, as indicated by bidirectional communications lines 58. The ginning process parameter measurements determined by the instruments 66 are time-stamped for correlation with time-stamped fiber quality data and the Permanent Bale Identification (PBI) number of each individual bale. Thus, for each bale, associated data includes both the fiber quality measurements determined by instrument 50 and the ginning process parameter measurements relevant to the processing of the cotton in the particular bale as determined by the instruments 66, with both sets of data relating to the time stamped moment or interval of production.

Also shown in FIG. 1, generally as a second element, is a database storage device 70, which stores a database 72 of bale identifications, for example Permanent Bale Identifications (PBIs), and associated fiber quality and ginning process parameter data, both time-stamped. The fiber quality data may include the currently-accepted qualities of Micronaire, Length, Strength, Color and Trash. Data representing additional fiber qualities may also be included such as, by way of example, moisture content, nep content, maturity, fineness and stickiness, as well as images. Ginning process data may include critical temperatures, process throughput, number and type of seed cotton and lint cleaners, and critical seed cotton and lint moisture contents.

Generally as a third element in the system of FIG. 1, as end users of cotton, are individual mills 80 and 82 which utilize the cotton to produce yarn then fabric. Associated with each of the mills 80 and 82 is a search engine/action engine 84, described in greater detail hereinbelow.

Other potential purchasers of cotton are merchants, represented in FIG. 1 by boxes 86 and 88. Similarly associated with each merchant 86 and 88 is combination search engine/action engine 84. Although merchants are not end users of cotton, merchants may purchase bales of cotton for eventual resale, or on behalf of, individual end users such as mills.

Elements of FIG. 1 are interconnected via a communications network 90, which may, for example, comprise the internet. In addition, portions of the communications network 90 may comprise other forms of communication links, such as local area networks and leased telephone lines. The database storage device 70 is connected to the communications network 90 as indicated by bidirectional arrow 92.

As indicated by bidirectional communications lines 94, the individual gin internal data networks 52 are connected via the communications network 90 to the database storage device 70 for uploading fiber quality data as measured by the fiber quality measurement instruments 50 and ginning process parameters as determined by instruments 66 to the database storage device 70 for storing in the database 72. Every time a bale of cotton is classed at the gin 22 or 24 using the instrument 50, fiber quality data are transferred into the ginner's internal network 52. The ginner releases that information to the database 72, along with the ginning process parameter data associated with particular bales by time stamps. The independent 30 and cooperative/subsidiary 32 warehouses also are connected by bidirectional communications lines 96 and 98 and via the communications network 90 to the database storage device 70.

The search engines/action engines 84 associated with the mills 80, 82 and merchants 86, 88 are also connected as indicated by bidirectional communication links 100 through the communications network 90 to the database storage device 70 to access the database 72. The search engines/action engines 84 are appropriately programmed computer systems. Depending upon the specific system architecture, the search engines/action engines 84 can be either programmed as part of the database storage device 70, which may take the exemplary form of an internet web server; or may be programmed as a part of a computer system local to the mill 80, 82 or merchant 86, 88; as examples. Thus FIG. 1 is exemplary only.

As also represented in the block diagram of FIG. 1, producers 102, in order to monitor bale production, fiber qualities, ginning process data, and market activity, are connected via a bidirectional communications link 104 and through the communications network 90 to the database storage device 70.

In simplified overview, described next are the elements and the transactions facilitated by the system 20 of FIG. 1. Following the simplified overview are descriptions of more sophisticated embodiments of the invention.

Figure 2:
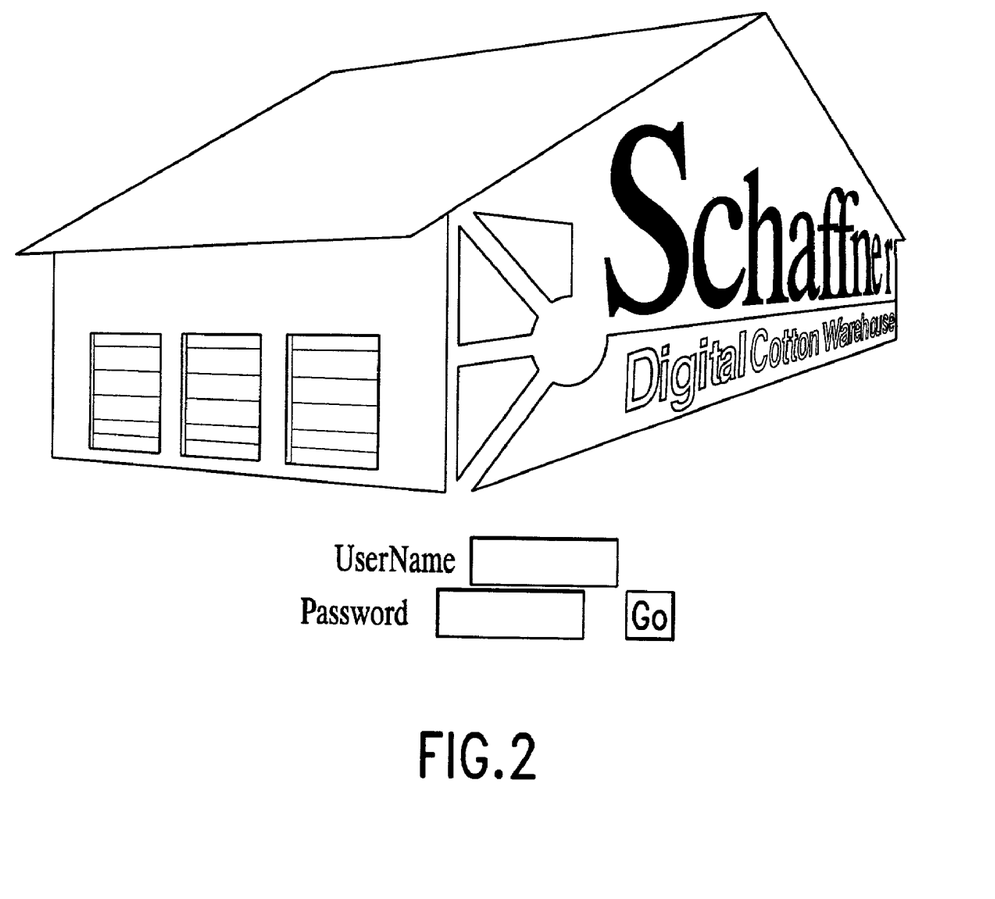
FIG. 2 is a screen image of an internet web page for entering a user name and password.

Referring to FIG. 2, which is a screen image of an Internet web page, underneath the Schaffner Digital Cotton Warehouse logo are spaces to enter a user name and password. The user types in a user name and password. A smart card technology may be employed for verification purposes.

Figure 3:
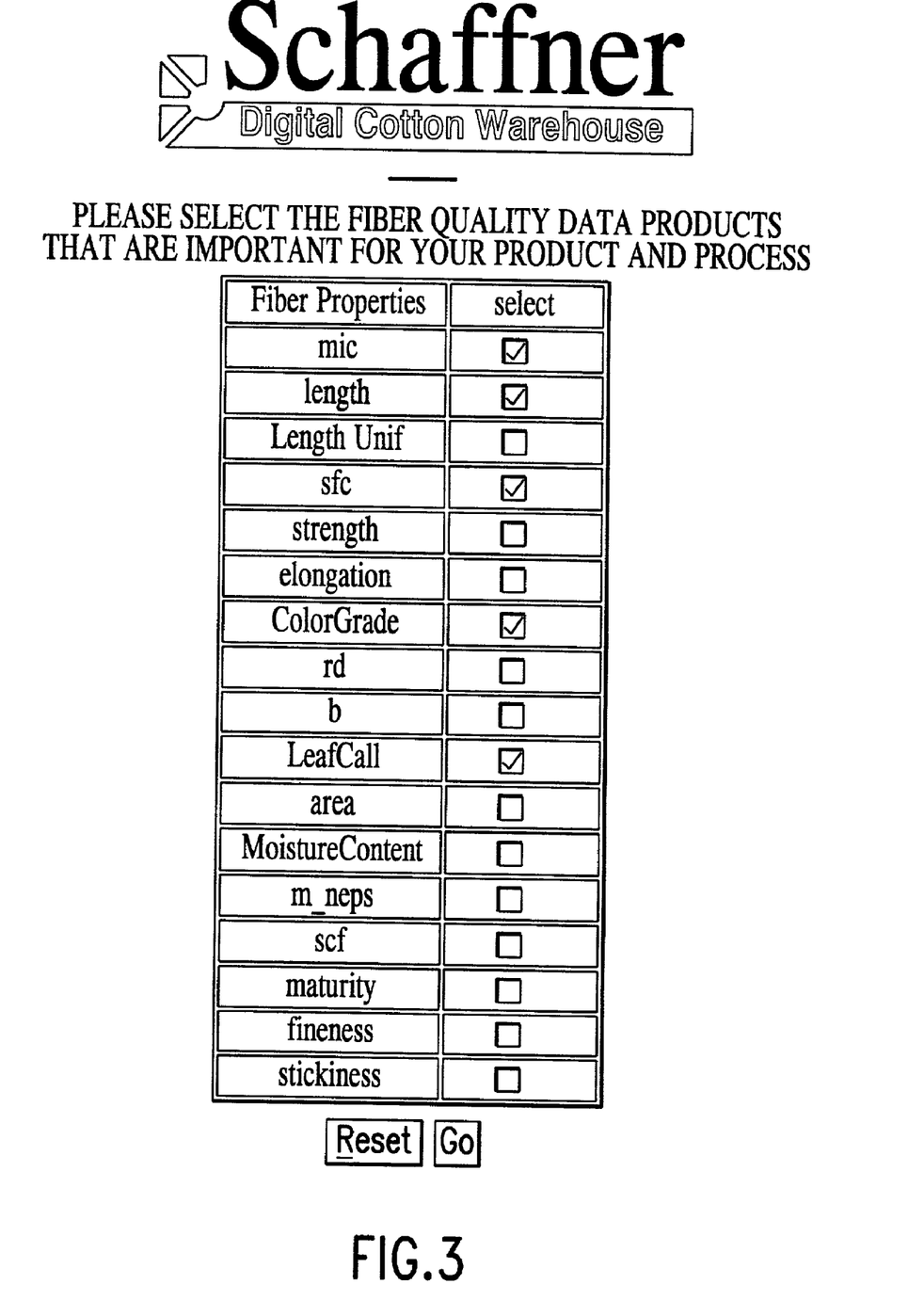
FIG. 3 is a screen image of an internet web page by which a user selects which fiber quality properties are of interest.

After the user is logged in, a second page (FIG. 3) is presented, which is a list of fiber qualities pertaining to cotton. The user selects those fiber properties which are of interest to match the raw material to processes and products. Thus, operators of the mills 80 and 82 know the product they are producing. For example, if a mill is producing a man's fine button down shirt, the mill would like a very fine, very long and strong cotton, and those respective fiber qualities would be selected. For simplicity, ginning process parameters are not shown in this particular example, but ginning process parameters can be included in the same manner.

Figure 4:
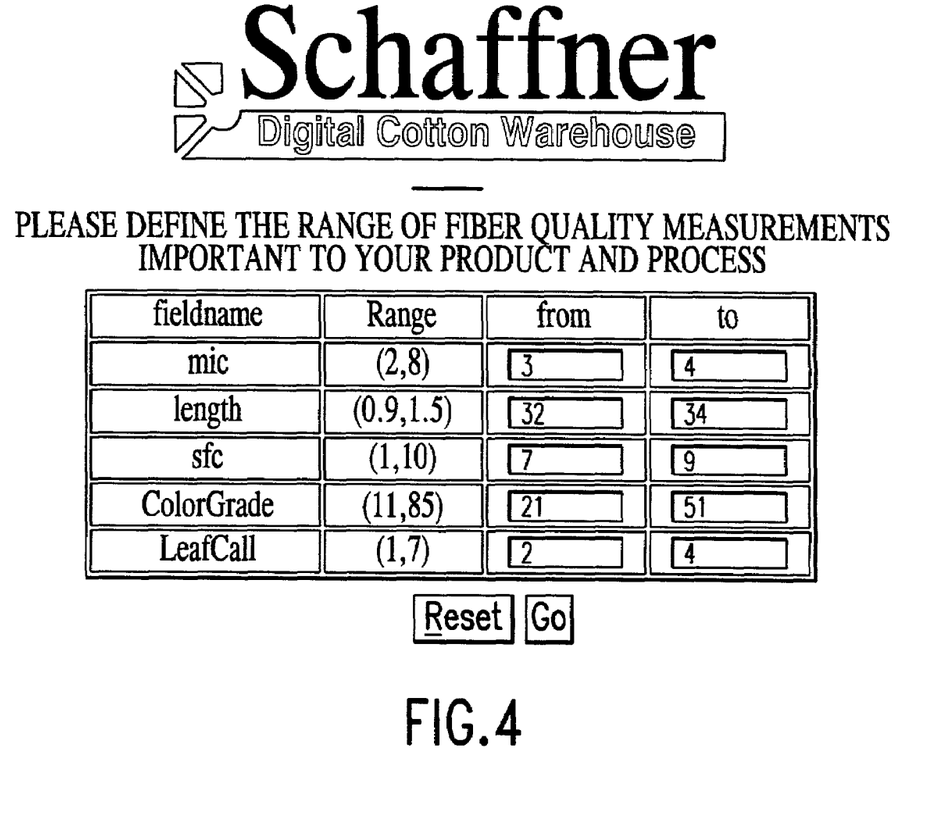
FIG. 4 is a screen image of an internet web page by which a user defines ranges of those fiber quality properties which are of interest.

The user selects "GO," and a third page (FIG. 4) is presented, which enables the user to define ranges for the fiber qualities previously selected to be of interest to the mill 80 or 82. After defining the ranges, the user selects "GO."

Figure 5:
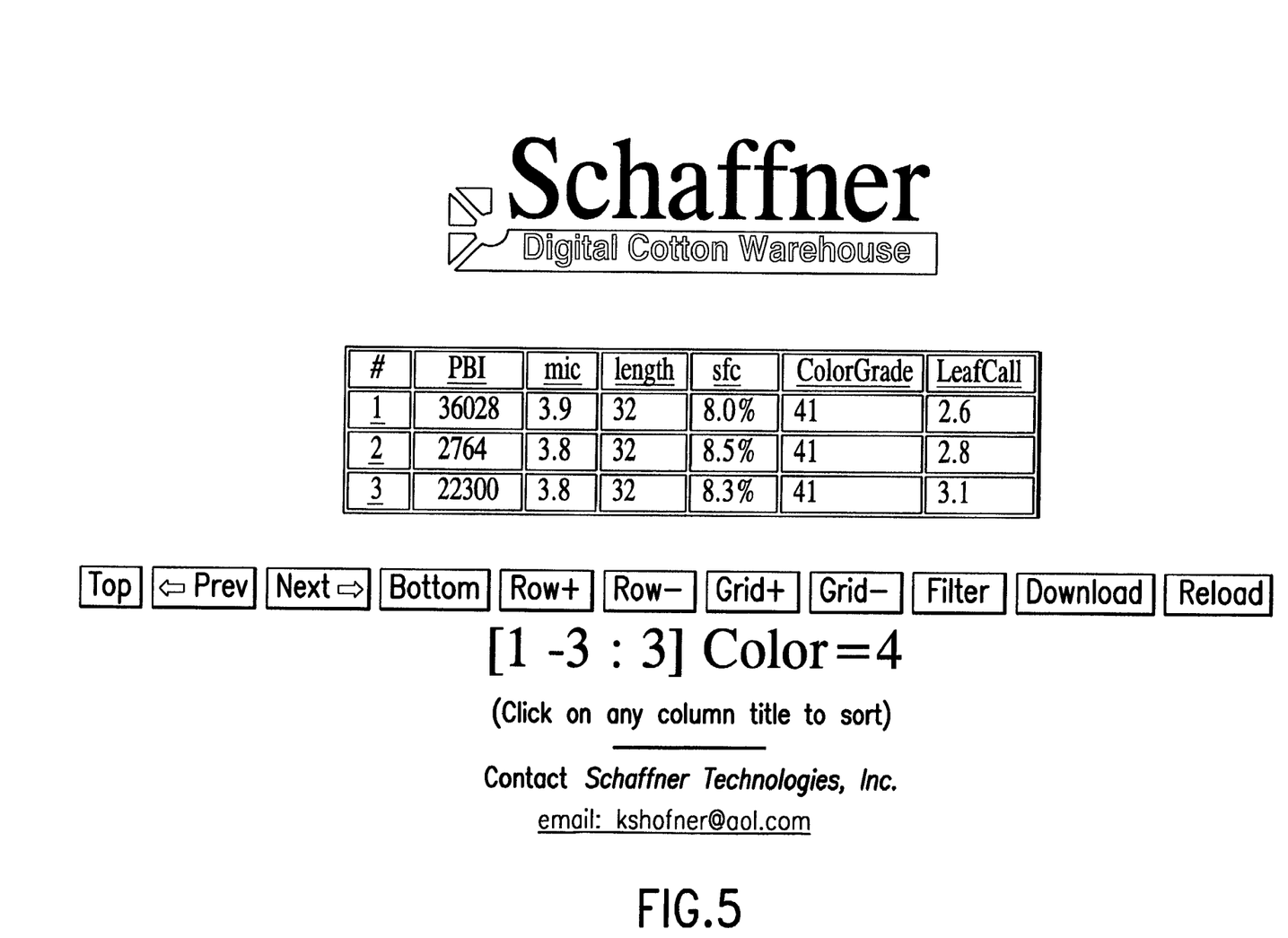
FIG. 5 is an image of an internet web page presenting the results of a database search.

The search engine 84 then accesses the database 72 and pulls out all relevant bales that meet the criteria. The fourth page (FIG. 5) is then presented. FIG. 5 is a grid of the Permanent Bale Identifications (PBIs), micronaire, length, strength, etc. listing all the relevant fiber properties that match those criteria. The user can click on either one on top, for example, Micronaire (mic), and the software orders it from the lowest to the highest. The same function applies to length as well as other properties. The bales are listed from the lowest length to the highest length. The user can keep on scanning through by selecting "next", which pulls up every bale that meets the criteria. There may be one, there may be 2,000. It's whatever the database 72 has in it.

Now if the user is interested in visually inspecting the cotton, clicking on the bale number (PBI) opens up the fifth page (FIG. 6), which is the cotton-specific image. Listed are the fiber qualities, along with a scanned image of the cotton, as well as a bar code and the fiber qualities of that specific cotton.

Figure 6:
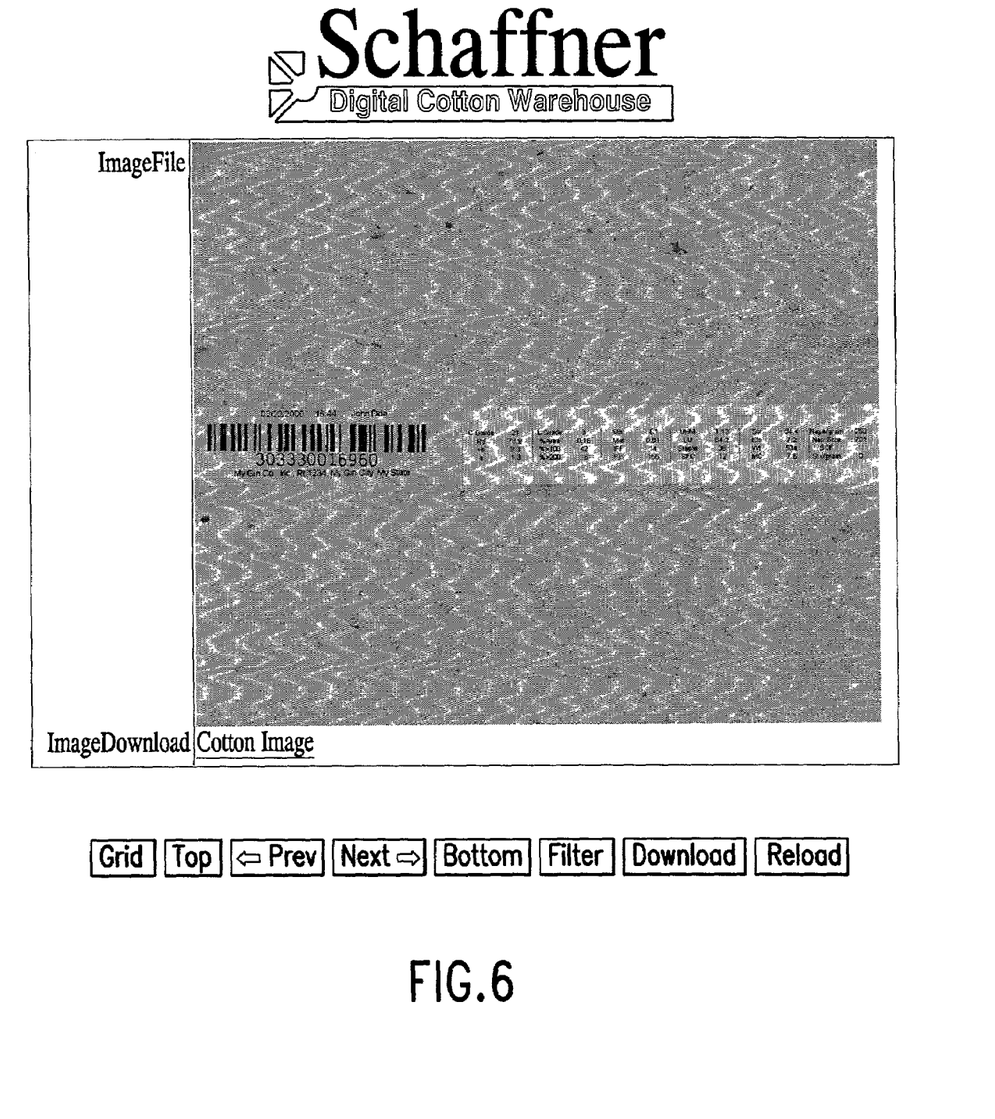
FIG. 6 is an image of an internet web page including an image of a sample bale.

The availability of images is a very powerful tool, and can aid arbitration, for example. So if there is ever a conflict users can see the bar code in the same image as the cotton. That bar code is unique: it defines the ginner and the producer.

Figure 7:
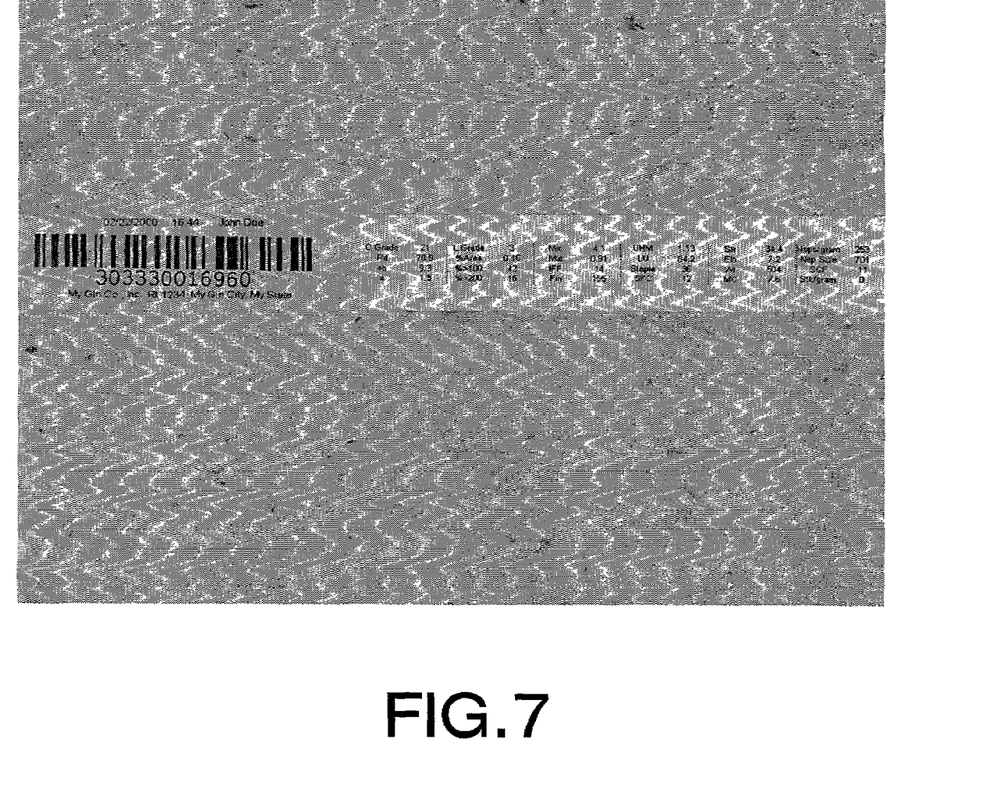
FIG. 7 is an enlarged image.

If the user is interested in examining the cotton in more detail, for example to determine types of trash (bark and grass, as examples) the user clicks on the cotton image and the image is magnified (FIG. 7).

After the user is satisfied with the bales that have been selected, they are put into a "shopping cart." Selecting "GO" creates a contract and removes those bales out of the Digital Cotton Warehouse, since those bales are no longer available for sale.

Locating the fiber quality measurement instrument 50 at the gin 22 or 24 for providing fiber quality substantially concurrently with the making up of cotton into individual bales, in combination with uploading the fiber quality data to the database storage device 70, provides a number of significant advantages. Again, as noted above, in conventional practice approximately four days elapse between the time when the bale is made up and fiber quality data are available so that marketing can occur.

In embodiments of the invention, fiber quality data and ginning process parameter data associated with the particular bale are uploaded to the database 72 within minutes of the baling operation, enabling marketing of the bale to begin immediately. Fiber quality data for a particular bale can be uploaded to the database 72 for immediate marketing literally even before the bale is wrapped in a protective covering. A mill 80, 82 or merchant 86, 88 can purchase bales even before they reach the warehouse 26, 28. Thus, as one example, bales being purchased by a particular mill 80, 82 or merchant 86, 88 can be accumulated in the warehouse 26, 28 in close proximity to each other, avoiding a subsequent physical search and retrieval operation. As another example, bales can even be loaded directly into trailers or containers for transport, bypassing the warehouse completely.

In another use of the invention, which can greatly reduce the cost of otherwise random retrieval even when bales are not purchased immediately following the bale press, with knowledge of the fiber qualities of a particular bale, similar bales are stored together in the warehouse, likely to be sold together as a lot. Thus, the bales of cotton are stored in the warehouse in agreed-upon groups with similar fiber quality.

In FIG. 1, the search engines/action engines 84, in addition to selecting bales having fiber qualities within specified ranges for a candidate buyer, operate to estimate the landed cost of fiber in bales selected by the search engine, and to initiate a buy action for an actual buyer. "Landed cost" is intended herein to mean the cost as delivered at the final customer, or end user.

Thus, in overview, the warehouses 26, 28, 30 and 32 and associated transportation elements, for transport of individual bales away from the bale press, as well as associated trailers for road transport, or containers for rail and/or sea transport, together comprise a transportation and storage system for transporting and storing individual bales of cotton after they are made up for optimized delivery to the actual buyer.

While only certain preferred features of the invention have been illustrated and described herein, many modifications and changes will occur to those skilled in the art. It is therefore to be understood that the appended claims are intended to cover all such modifications and changes as fall within the true spirit and scope of the invention.

What is claimed is:

1. A computer-implemented system for building a database of data describing individual bales of cotton available for sale, comprising:

a database storage device connected to a communications network for storing a database of bale identifications and associated fiber quality data; and a fiber quality measurement instrument located in a cotton gin for providing fiber quality data on bale classing samples cut from individual bales at a bale press substantially concurrently with the making up of cotton into individual bales, and connected to said communications network for uploading to said database storage device.

2. The system of claim 1, which further comprises at least one ginning process parameter measurement instrument located in the cotton gin, and wherein the database storage device further stores associated ginning process parameter data.

3. The system of claim 1, wherein said fiber quality measurement instrument measures one or more of micronaire, length, strength, color, trash, moisture content, nep content, maturity, fineness and stickiness.

4. The system of claim 1, wherein said fiber quality measurement instrument acquires images of bale classing samples from individual bales for uploading to said database storage device.

5. The system of claim 3, wherein said fiber quality measurement instrument acquires images of bale classing samples from individual bales for uploading to said database storage device.

6. The system of claim 2, wherein the at least one ginning process parameter measurement instrument measures one or more of critical temperatures, process throughput, number and type of seed cotton cleaners, number and type of lint cleaners, seed cotton moisture content, and lint moisture content.

7. The system of claim 1 wherein said database stores, as each bale identification, an individual Permanent Bale Identification (PBI) number.

8. A computer-implemented system for electronic commerce of bales of cotton, comprising:

a database storage device connected to a communications network for storing a database of data describing individual bales of cotton, in particular, bale identifications and associated fiber quality data;

a fiber quality measurement instrument located in a cotton gin for providing fiber quality data on bale classing samples cut from individual bales at a bale press substantially concurrently with the making up of cotton into individual bales, and connected to said communications network for uploading to said database storage device; and a search engine connected via said communications network to interrogate the database to select bales having fiber qualities within specified ranges for a candidate buyer.

9. The system of claim 8, which further comprises at least one ginning process parameter measurement instrument located in the cotton gin, and wherein the database further stores associated ginning process parameter data.

10. The system of claim 8, wherein each bale has a corresponding landed cost, and which system further comprises an action engine that estimates the landed cost of fiber in bales selected by said search engine and initiates a buy action for an actual buyer.

11. The system of claim 10, which further comprises a transportation and storage system for transporting and storing individual bales of cotton after they are made up for optimized delivery to the actual buyer.

12. The system of claim 8, wherein said fiber quality measurement instrument measures one or more of micronaire, length, strength, color, trash, moisture content, nep content, maturity, fineness and stickiness.

13. The system of claim 8, wherein said fiber quality measurement instrument acquires images of bale classing samples from individual bales for uploading to said database storage device.

14. The system of claim 12, wherein said fiber quality measurement instrument acquires images of bale classing samples from individual bales for uploading to said database storage device.

15. The system of claim 9, wherein the at least one ginning process parameter measurement instrument measures one or more of critical temperatures, process throughput, number and type of seed cotton cleaners, number and type of lint cleaners, seed cotton moisture content, and lint moisture content.

16. The system of claim 8 wherein said database stores, as each bale identification, an individual Permanent Bale Identification (PBI) number.

17. A computer-implemented method for building a database of bales of cotton available for sale, comprising the steps of:
employing a fiber quality measurement instrument located in a cotton gin to provide fiber quality data on bale classing samples cut from individual bales at a bale press substantially concurrently with the making up of cotton into individual bales; and
transmitting the fiber quality data via a communications network to a database storage device that stores a database of bale identifications and associated fiber quality data.

18. The method of claim 17, which further comprises employing at least one ginning process parameter measurement instrument located in the cotton gin to provide ginning process parameter data, and transmitting the ginning process parameter data via the communications network to the database storage device, the database storage device storing associated ginning process parameter data with bale identifications.

19. The method of claim 17, wherein said step of employing a fiber quality measurement instrument comprises employing an instrument that measures one or more of micronaire, length, strength, color, trash, moisture content, nep content, maturity, fineness and stickiness.

20. The method of claim 17, which further comprises acquiring images of bale classing samples from individual bales, and digitally transmitting the images to the database storage device.

21. The method of claim 19, which further comprises acquiring images of bale classing samples from individual bales, and digitally transmitting the images to the database storage device.

22. The method of claim 18, wherein the ginning process parameter data includes one or more of critical temperatures, process throughput, number and type of seed cotton cleaners, number and type of lint cleaners, seed cotton moisture content, and lint moisture content.

23. The system of claim 17 wherein said database stores, as each bale identification, an individual Permanent Bale Identification (PBI) number.

24. A computer-implemented method for electronic commerce of bales of cotton, comprising the steps of:
employing a fiber quality measurement instrument located in a cotton gin to provide fiber quality data on bale classing samples cut from individual bales at a bale press substantially concurrently with the making up of cotton into individual bales;
transmitting the fiber quality data via a communications network to a database storage device that stores a database of bale identifications and associated fiber quality data; and
employing a search engine connected via the communications network to interrogate the database to select bales having fiber qualities within specified ranges for a candidate buyer.

25. The method of claim 24, which further comprises employing at least one ginning process parameter measurement instrument located in the cotton gin to provide ginning process parameter data, and transmitting the ginning process parameter data via the communications network to the database storage device, the database storage device storing associated ginning process parameter data with bale identifications.

26. The method of claim 24, wherein each bale has a corresponding landed cost, and which method further comprises employing an action engine that estimates the landed cost of fibers in bales selected by the search engine and initiates a buy action for an actual buyer.

27. The method of claim 26, which further comprises transporting and storing individual bales of cotton after they are made up for optimized delivery to the actual buyer.

28. The method of claim 24, wherein said step of employing a fiber quality measurement instrument comprises employing an instrument that measures one or more of micronaire, length, strength, color, trash, moisture content, nep content, maturity, fineness and stickiness.

29. The method of claim 24, which further comprises acquiring images of bale classing samples from individual bales, and digitally transmitting the images to the database storage device.

30. The method of claim 28, which further comprises acquiring images of bale classing samples from individual bales, and digitally transmitting the images to the database storage device.

31. The method of claim 25, wherein the ginning process parameter data includes one or more of critical temperatures, process throughput, number and type of seed cotton cleaners, number and type of lint cleaners, seed cotton moisture content, and lint moisture content.

32. The method of claim 24 wherein said database stores, as each bale identification, an individual Permanent Bale Identification (PBI) number.

* * * * *